United States Patent [19]
Cadot et al.

[11] Patent Number: 5,330,954
[45] Date of Patent: Jul. 19, 1994

[54] CATALYTIC SYSTEM AND ITS APPLICATION TO THE OXYDEHYDROGENATION OF SATURATED CARBOXYLIC ACIDS AND THE OXIDATION OF ALDEHYDES TO ACIDS

[75] Inventors: Emmanuel Cadot, Gentilly; Franck Daubrege, Paris; Gilbert Herve, Levis Saint Nom; André Teze, Conflans St. Honorine, all of, France

[73] Assignee: Elf Atochem, S.A., Paris, France

[21] Appl. No.: 939,510

[22] Filed: Sep. 3, 1992

[30] Foreign Application Priority Data

Sep. 30, 1991 [FR] France .................. 91 10868

[51] Int. Cl.[5] .................. B01J 27/198; C07C 51/16
[52] U.S. Cl. .................. 502/209; 562/531; 562/532; 562/535; 562/599; 502/211
[58] Field of Search .................. 502/209, 20; 562/531, 562/532, 535, 599

[56] References Cited

U.S. PATENT DOCUMENTS

| | | | |
|---|---|---|---|
| 4,146,574 | 3/1979 | Onoda et al. | 502/209 X |
| 4,565,801 | 1/1986 | Shimizu et al. | 502/209 |
| 4,720,575 | 1/1988 | Gruber | 502/209 X |

FOREIGN PATENT DOCUMENTS

| | | |
|---|---|---|
| 0255639 | 7/1987 | European Pat. Off. . |
| 0284947 | 3/1988 | European Pat. Off. . |
| 2407022 | 10/1978 | France . |

*Primary Examiner*—Asok Pal
*Assistant Examiner*—P. Achutamurthy
*Attorney, Agent, or Firm*—Millen, White, Zelano & Branigan

[57] ABSTRACT

A catalytic system based on oxygen, vanadium, phosphorus, and molybdenum corresponding to the formula $H_mX_nMe_pPMo_{12-x}V_xO_{40}$, wherein X represents the $VO^{2+}$ cation with $0 < n \leq 2$, H represents protons with $0 \leq m < 4$, $0 \leq x \leq 3$, Me is a metal ion, especially an ion of a transition metal, with $0 \leq p \leq t$, t depending on the charge of the corresponding ion, is useful for the oxydehydrogenation of saturated carboxylic acids to $\alpha,\beta$-unsaturated acids and for oxidizing aldehydes to acids.

30 Claims, No Drawings

CATALYTIC SYSTEM AND ITS APPLICATION TO THE OXYDEHYDROGENATION OF SATURATED CARBOXYLIC ACIDS AND THE OXIDATION OF ALDEHYDES TO ACIDS

BACKGROUND OF THE INVENTION

The present invention relates to a catalytic system based on molybdenum, phosphorus, vanadium and oxygen; it has more particularly for its subject a catalytic system consisting of a heteropolyanion to which are connected, in variable proportions, cations such as protons $H^+$, the vanadyl cation $VO^{2+}$ or metal cations such as copper: $Cu^{2+}$, iron: $Fe^{3+}$ or cobalt $Co^{2+}$. The catalytic system which is the subject of the invention is particularly suitable for the oxydehydrogenation reaction of saturated carboxylic acids or esters to the corresponding unsaturated acids or esters, in particular for the oxydehydrogenation reaction of isobutyric acid to methacrylic acid, as well as for oxidation reactions such as the oxidation of methacrolein to methacrylic acid.

Catalytic systems have been known for a long time which make it possible to carry out the oxydehydrogenaion of saturated carboxylic acids or esters to the corresponding unsaturated acids or esters. Thus, there is described in French Pat. No. 2,497,795 a catalyst of general formula: $FeP_xMe_yO_z$, in which Me is Li, Na, K, Rb, Cs, Mg, Sr or Ba: such a catalyst is suitable for the manufacture of methacrylic acid from isobutyric acid. The synthesis of methacrylic acid from isobutyric acid in the presence of a binary mixture of oxides consisting of vanadium oxide ($V_2O_5$) and phosphorus pentoxide ($P_2O_5$) has also been described (J. Catal. 98, 401, 1986). In this same publication, comparative tests were also carried out starting from catalysts of formula $H_5PMo_{10}V_2O_{40}$. The results indicated show that the selectivity towards methacrylic acid levels out at around 60 % whatever the catalyst used.

Catalytic systems based on heteropolyanions have also been described in other publications as catalysts for the oxidising dehydrogenation reaction of isobutyric acid, or of its esters, to methacrylic acid or to its esters.

Thus, German Application (DOS) 2,722,375 describes catalysts obtained by concentration of an aqueous solution of a heteropolyacid of composition $H_5PMo_{10}V_2O_{40}$ and of a copper salt, optionally in the presence of an alkali metal salt, the dry residue then being calcined. Such catalysts make it possible to achieve selectivities towards methacrylic acid of 71–72 % and, by incorporation of lithium, it is possible to achieve 74.8 %.

U.S. Pat. No. 4,307,247 proposes, for the same oxidising dehydrogenation reaction, catalysts based on molybdenum, vanadium, copper, phosphorus and bismuth, to which an alkali metal of the potassium, rubidium or caesium group, and optionally other metals, is added as well as oxygen in determined quantitative ratios.

U.S. Pat. No. 4,314,075 proposes, for the same reaction, similar catalysts based on the following elements: molybdenum, vanadium, copper and phosphorus and an alkali metal chosen from potassium, rubidium or caesium and one or more other metals as well as oxygen in determined quantitative ratios. All metals are present during the hydrothermal reaction which leads to the aqueous solution of a heteropolyanion. The selectivities for methacrylic acid achieved in the presence of these catalysts are between 60 and 70 %.

U.S. Pat. No. 4,522,934 also describes catalysts for this oxydehydrogenation reaction, of general formula $H_{3+x}PV_xW_{3-x}Mo_9O_{40}$ with $0<x<3$. The system $H_{3.5}PMo_9V_{0.5}W_{2.5}O_{40}$, supported on silica, makes it possible to achieve a conversion of isobutyric acid of 93 % and a selectivity for methacrylic acid of 79 %.

All these catalytic systems derived from heteropolyanions, however, exhibit the general drawback of having a limited stability over time under the oxydehydrogenation reaction conditions.

It is also recorded in the prior art that this type of catalyst can be used to carry out the oxygenation of methacrolein to methacrylic acid with good yields. Proc. 7th Intern. Congress Catalysis, Tokyo (1980), p. 755.

It is thus felt necessary to have available catalysts of the heteropolyanion type which make it possible to obtain selectivities towards unsaturated carboxylic acids which are industrially acceptable in combination with high conversions of the starting saturated carboxylic acids which are subjected to the catalytic oxydehydrogenation reaction; these catalysts must also exhibit good degrees of conversion of aldehydes in the oxidation reactions of aldehydes to acids, in particular during the oxidation of methacrolein to methacrylic acid. Moreover, it is also necessary that these catalysts remain stable over time under the reaction conditions.

SUMMARY OF THE INVENTION

The subject of the present invention is a catalytic system based on oxygen, vanadium, phosphorus and molybdenum, characterised in that the catalytic system corresponds to the general formula: $H_mX_nMe_pPMo_{12-x}V_xO_{40}$ in which X represents the $VO^{2+}$ cation with $0<n\leq 2$.

H represents a proton with $0\leq m<4$, $0\leq x\leq 3$, Me is a metal ion, in particular a transition metal ion, with $0\leq p<t$, t depending on the charge of the corresponding ion. For example, t is equal to 2 for copper and cobalt, and is equal to 1.333 for iron. In particular, $m+2n+qp=4$, q being the charge on the Me ion.

According to the invention, the catalytic systems have the formula $H_mX_nMe_pPMo_{12-x}V_xO_{40}$, in which Me is a metal ion, in particular an ion of a transition metal such as copper, cobalt, iron, silver, nickel, or manganese. Me can also represent an alkali metal or magnesium.

The invention also relates to a process for the manufacture of the catalytic system which has just been defined, according to which the heteropolyacid $H_4PMo_{12-x}V_xO_{40}$ is prepared in a manner known per se and the $VO^{2+}$ cation and, if appropriate, at least one Me cation are then introduced, especially by reaction with barium hydroxide and vanadyl sulphate and, if appropriate, one or more sulphates of one or more Me cations are introduced, with precipitation of barium sulphate and, if appropriate, the catalytic system sought after is prepared from the heteropolyacid compound obtained in the preceding stage, by substitution of at least a part of the protons by reaction with a carbonate or hydroxide of the corresponding Me cation(s) to be combined.

The catalytic systems which are the subject of the invention are thus advantageously manufactured in two stages. In a first stage, the heteropolyacid of formula $H_4PMo_{11}VO_{40}$ (see Courtin, Rev de Chimie Minérale 8, 75, 1971) is manufactured in a known way or, in a more general way, the heteropolyacid of formula $H_4PMo_{12-x}V_xO_{40}$.

1) Preparation of the heteropolyacid of formula $H_4PMo_{11}VO_{40}$

Sodium metavanadate ($NAVO_3$) and sodium monohydrogenphosphate dihydrate are mixed in equimolecular quantities and acidified with hydrochloric acid. Sodium molybdate ($Na_2MoO_4$) (11 moles per 1 mole of preceding reactants) is then added and the reaction mixture is acidified with hydrochloric acid. The solution is then treated with ether, separated and crystallised.

2) Introduction of cations ($VO^{2+}$ and, if appropriate, $CU^{2+}$, $Fe^{3+}$, $Co^{2+}$, and the like)

The heteropolyacid is dissolved in water and then n moles of solid barium hydroxide ($Ba(OH)_2 \cdot 8H_2O$) and n moles of vanadyl sulphate ($VOSO_4 \cdot 5H_2O$) are added per 1 mole of this heteropolyacid. It is possible to replace a part of the vanadyl sulphate with one or more sulphates of the Me cation(s) to be introduced, this being a function of the number of protons which it is wished to substitute in the heteropolyacid as well as of the nature of the cation, in order to obtain the desired general formula. The barium sulphate formed is then removed by filtration and the catalytic composition is extracted by crystallisation or by evaporation.

From the compounds $H_{4-2n}(VO)_nPMO_{11}VO_{40}$, where $0 < n \leq 2$, it is possible to obtain certain compounds $H_m(VO)_nMe_pPMo_{11}VO_{40}$ where Me is a metal cation such as $Cu^{2+}$ or $Co^{2+}$ by substitution of the protons with a carbonate or hydroxide salt of the corresponding cation to be combined. The preparation is then carried out in the following way: one part of the carbonate of the cation to be combined is added, in a quantity corresponding to the desired formula, to one part of $H_{4-2n}(VO)_nPMO_{11}VO_{40}$ dissolved in distilled water. The extraction of the solid compound is then carried out by evaporation, as above.

The subject of the present invention is also a process for oxydehydrogenation of saturated carboxylic acids in order to form α,β-unsaturated carboxylic acids. This process consists in bringing the saturated carboxylic acids into contact with molecular oxygen or a gas containing oxygen and, if appropriate, an inert diluent gas in the vapour phase, at a reaction temperature of between 280° C. and 400° C., preferably between 300° and 340° C., in the presence of a catalytic system comprising a catalyst of general formula $H_mX_nMe_pPMo_{12-x}V_xO_{40}$, in which m, n, p and x have the abovementioned values, in a molar ratio to the saturated acid which does not exceed 2. This reaction is preferably carried out in the presence of water vapour, which allows the reaction to progress well.

This type of reaction generally takes place in a fixed bed tubular reactor, the general operation of which may be described by the theoretical model of the piston reactor. The operating conditions in such a circuit are generally the following: a charge conveyed onto the catalyst, which is previously formulated (pellets, extrudate) or deposited on a suitable substrate, comprises a generally preheated gaseous mixture consisting of saturated acid, molecular oxygen, water and an inert gaseous diluent (such as nitrogen or helium). The proportion of acid in this mixture is generally between 1 and 8%, expressed in moles, the proportion of molecular oxygen is, in moles, 0.2 to 5 times greater than that of the saturated acid, preferably from 0.5 to 2. The water introduced into the reactor, with a molar ratio between 0 and 15 with respect to the saturated acid, is of course understood as excluding the quantity of water generated, as is well known, by the actual oxidising dehydrogenation reaction. The contact time between the charge and the catalyst is between 0.1 and 50 seconds and preferably between 0.2 and 4 seconds.

Another subject of the present invention consists in the employment of the catalysts in the oxidation reaction of methacrolein to methacrylic acid. This reaction is carried out in a conventional way under the same operating conditions as the oxydehydrogenation reaction of saturated carboxylic acids.

The following examples illustrate the present invention.

EXAMPLE 1

Catalyst used $VOH_2PMO_{11}VO_{40}$

A solution containing 0.1 mol of sodium metavanadate $NaVO_3$ in 0.5 dm$^3$ of water and 0.1 mol of sodium monohydrogenphosphate dihydrate (17.8 g) is acidified with 0.12 mol of hydrochloric acid (10 ml of 35 % HCl). A solution consisting of 1.1 mol of sodium molybdate dihydrate (266 g) diluted in 0.5 dm$^3$ of water is added dropwise to this solution. The solution thus obtained is acidified with 4.5 mol of hydrochloric acid (400 ml of 35 % HCl). After cooling this solution, 400 ml of diethyl ether are added. After settling out (three phases), a heavy layer which contains the desired compound is recovered (200 ml) to which 100 ml of water are added. The ether is removed from the solution by stirring in air. The compound is extracted from the final solution by crystallisation at 4° C. The crystals thus obtained of formula $H_4PMo_{11}VO_{40} \cdot 29H_2O$ effloresce rapidly in air to give $H_4PMo_{11}VO_{40} \cdot 13H_2O$. The yield of heteropolyacid is 97 % with respect to the compounds used.

10 g of $H_4PMo_{11}VO_{40}$ ($4.95 \times 10^{-3}$ mol) are dissolved in 10 ml of distilled water, 1.56 g of $Ba(OH)_2 \cdot 8H_2O$ ($4.95 \times 10^{-3}$ mol) is slowly added to the solution in small portions with stirring and 1.25 g of $VOSO_4 \cdot 5H_2O$ ($4.95 \times 10^{-3}$ mol) is then introduced. A barium sulphate precipitate appears and is removed by filtration. This precipitate is washed several times with small portions of distilled water. The wash liquors are collected and added to the mother solution. 10 g of $VOH_2PMo_{11}V_{40}$ are extracted from the solution by evaporation of the water by nitrogen sparging for three hours at room temperature or by evaporation on a rotary evaporator under vacuum with moderate heating at 60° C.

0.66 gram of the catalyst thus obtained is introduced into a fixed bed tubular reactor. A thermal pretreatment of this catalyst is carried out under a flow of air, with a heating rate of 225° C./h for one hour to reach 250° C. and to keep at this temperature for 2 hours before causing it to undergo a temperature increase from 250 ° C. to 320° C. over 1 hour.

The following reaction mixture is introduced into the same reactor:
2.2 % in moles of isobutyric acid
5.2 % in moles of molecular oxygen
3.8 % in moles of water vapour
88.8 % in moles of diluent nitrogen.

The flow rate of the gaseous mixture is 165 ml/minute, which represents a passage time of the gas with respect to the volume of the introduced catalyst of 0.2 second, and the temperature in the reactor is 320° C. The results obtained are listed in Table 1.

EXAMPLE 2

Catalyst used: $(VO)_{0.5}H_3PMo_{11}VO_{40}$ 10 g of $H_4PMo_{11}VO_{40}$ ($4.95\times10^{-}$mol), obtained according to the method described above, are dissolved in 10 ml of distilled water. 0.78 gram of $Ba(OH)_2\cdot 8H_2O$ ($2.5\times10^{-3}$ mol) is slowly added in small portions to the solution with stirring and then 0.625 g of $VOSO_4\cdot 5H_2O$ ($2.5\times10^{-3}$ mol) is added. A barium sulphate precipitate appears and is removed by filtration. This precipitate is washed several times with small portions of distilled water. The wash liquors are collected and added to the filtered mother solution. 10 g of $(VO)_{0.5}H_3PMo_{11}VO_{40}$ are extracted by evaporation as in Example 1.

The catalytic performances of this system, for the oxydehydrogenation of isobutyric acid, are evaluated in an identical manner to that described in Example 1. The results are collated in Table 2.

EXAMPLE 3

Catalyst used: $(VO)_2PMo_{11}VO_{40}$ 10 g of $H_4PMo_{11}VO_{40}$ ($4.95\times10^{-3}$ mol) are dissolved in 10 ml of distilled water, 3.12 g of $Ba(OH)_{2b}\cdot 8H_2O$ ($9.9\times10^{-3}$ mol) are then slowly added in small portions to the solution with stirring and then 2.5 g of $VOSO_4\cdot 5H_2O$ ($9.9\times10^{-3}$ mol) are added. A barium sulphate precipitate appears which is removed by filtration. This precipitate is washed several times with small portions of distilled water. The wash liquors are collected and added to the filtered mother solution. 10 g of $(VO)_2PMo_{11}VO_{40}$ are extracted by evaporation as in Example 1.

The catalytic performances of this system, for the oxydehydrogenation of isobutyric acid, are evaluated in an identical manner to that described in Example 1. The results are collated in Table 3.

EXAMPLE 4

Catalyst used: $(VO)_{1.5}Cu_{0.5}PMo_{11}VO_{40}$ 10 g of $H_4PMo_{11}VO_{40}$ ($4.95\times10^{-3}$ mol), obtained according to the method described above, are dissolved in 10 ml of distilled water, 3.12 g of $Ba(OH)_2\cdot 8H_2O$ ($9.9\times10^{-3}$ tool) are slowly added in small portions to the solution with stirring and then 1.875 g of $VOSO_4\cdot 5H_2O$ ($7.5\times10^{-3}$ mol) and 0.624 g of $CuSO_4\ 5H_2O$ ($2.5\times10^{-3}$ mol) are introduced. A barium sulphate precipitate appears which is removed by filtration. This precipitate is washed several times with small portions of distilled water. The wash liquors are collected and added to the filtered mother solution. 10 g of $(VO)_{1.5}Cu_{0.5}PMo_{11}VO_{40}$ are extracted by evaporation as in Example 1.

The catalytic performances of this system, for the oxydehydrogenation of isobutyric acid, are evaluated in an identical manner to that described in Example 1 with a following composition of the reaction gas:

2.2 % in moles of isobutyric acid
2.8 % in moles of molecular oxygen
3.8 % in moles of water vapour
91.2 % in moles of diluent nitrogen.

The results are collated in Table 4.

EXAMPLE 5

Catalyst used: $VOHCu_{0.5}PMo_{11}VO_{40}$ 10 g of $H_4PMo_{11}VO_{40}$ ($4.95\times10^{-3}$ mol) are dissolved in 10 ml of distilled water and 1.56 g of $Ba(OH)_2 8H_2O$ ($4.95\times10^{-3}$ mol) is slowly added in small portions to the solution with stirring and then 1.25 g of $VOSO_4\cdot 5H_2O$ ($4.95\times10^{-3}$ mol) is added. A barium sulphate precipitate appears which is removed by filtration. This precipitate is washed several times with small portions of distilled water. The wash liquors are collected and added to the filtered mother solution. 10 g of $VOH_2PMo_{11}VO_{40}$ are extracted from the solution by evaporation of the water with nitrogen sparging for 3 hours at room temperature or by evaporation in a rotary evaporator under vacuum with moderate heating at 60 ° C.

0.232 g of $CuCO_3\cdot Cu(OH)_2$ ($1.05\times10^{-3}$ mol) is added to 10 g ($4.2\times10^{-3}$ mol) of this system dissolved in 10 ml of distilled water. 10 g of $VOHCu_{0.5}PMo_{11}VO_{40}$ are extracted by evaporation as in Example 1.

The catalytic performances of this system, for the oxydehydrogenation of isobutyric acid, are evaluated in an identical manner to that described in Example 1. The results are collated in Table 5.

EXAMPLE 6

Catalyst used: $VOHCo_{0.5}PMo_{11}VO_{40}$ 10 g of $H_4PMo_{11}VO_{40}$ ($4.95\times10^{-3}$ mol) are dissolved in 10 ml of distilled water and 1.56 g of $Ba(OH)_2\cdot 8H_2O$ ($4.95\times10^{-3}$ mol) is slowly added in small portions to the solution with stirring and then 1.25 g of $VOSO_4\cdot 5H_2O$ ($4\ 95\times10^{-3}$ mol) are added. A barium sulphate precipitate appears which is removed by filtration. This precipitate washed several times with small portions of distilled water, The wash liquors are collected and added to the filtered mother solution. 10 g of $VOH_2PMo_{11}VO_{40}$ are extracted from the sobrios by evaporation of the water by nitrogen 8parging for 3 hours at room temperature or by evaporation in a rotary evaporator under vacuum with moderate heating at 60° C.

0.250 g of $CoCO_3$ ($2.1\times10^{-3}$ mol), in the form of the corresponding quantity of hydrated cobalt carbonate, is added to 10 g ($4.2\times10^{-3}$ mol) of this system dissolved in 10 ml of distilled water. 10 g of $VOHCo_{0.5}PMo_{11}VO_{40}$ are extracted by evaporation as in Example 1.

The catalytic performances of this system, for the oxydehydrogenation of isobutyric acid, are evaluated in an identical manner to that described in Example 1. The results are collated in Table 6.

EXAMPLE 7

Catalyst used: $VOHFe_{0.33}PMo_{11}V_{40}$ 10 g Of $H_4PMo_{11}VO_{40}$ ($4.95\times10^{-3}$ mol) are dissolved in 10 ml of distilled water and 1.56 g of $Ba(OH)_2\cdot 8H_2O$ ($4.95\times10^{-3}$ mol) is slowly added in small portions to the solution with stirring and then 1.25 g of $VOSO_4\cdot 5H_2O$ ($4.95\times10^{-3}$ mol) is added. A barium sulphate precipitate appears which is removed by filtration. This precipitate is washed several times with small portions of distilled water. The wash liquors are collected and added to the filtered mother solution. 10 g of $VOH_2PMo_{11}VO_{40}$ are extracted from the solution by evaporation of the water with nitrogen sparging for 3 hours at room temperature or by evaporation in a rotary evaporator under vacuum with moderate heating at 60° C.

10 g of this system ($4.2 \times 10^{-3}$ mol), dissolved in 10 ml of distilled water, are stirred with freshly precipitated ferric hydroxide ($1.4 \times 10^{-3}$ mol). This ferric hydroxide is obtained from 0.57 g of iron(III) nitrate containing 9 molecules of water, which is dissolved, precipitated in an ammoniacal medium, filtered and washed.

The catalytic performances of this system, for the oxydehydrogenation of isobutyric acid, are evaluated in an identical manner to that described in Example 1. The results are collated in Table 7.

EXAMPLE 8

The system $VOH_2PMo_{11}VO_{40}$ is calcined at 120° C. for 3 hours and then pelletised. 25 grams of the ring-shaped pellets thus obtained, diluted in silicon carbide, are introduced into a reactor heated with a salt bath at 200° C. The temperature of the salt bath is then increased from 250° to 300° C. over one hour and then a liquid and gaseous reaction mixture, after passing over a vaporiser at 200° C., is introduced into the reactor.

The reaction mixture consists of:
2.2 % in moles of isobutyric acid
5.2 % in moles of molecular oxygen
3.8 % in moles of water vapour
88.8 % in moles of diluent nitrogen.

The catalytic performances of this system, for the oxydehydrogenation of isobutyric acid, are evaluated in an identical manner to that described in Example 1. The results are collated in Table 8.

EXAMPLE 9

Oxidation of methacrolein to methacrylic acid:

Catalyst used: $VOHCu_{0.5}PMo_{11}V_{40}$

A reaction mixture is used, in a reactor, which consists in moles of:
3 % of methacrolein
13.4 % of air
53.6 % of nitrogen
20 30 % of water.

The reaction is carried out at atmospheric pressure at 310° C., and the passage time of the gas with respect to the volume of the catalyst is 2.4 seconds.

The conversion of methacrolein is 90 % and the selectivity for methacrylic acid is 75 %.

TABLE 1

| TIME hours | CONVERSION % | MAA SELECTIVITY % | PROPENE SELECTIVITY % | ACETONE SELECTIVITY % | ACETIC ACID SELECTIVITY % | $CO/CO_2$ SELECTIVITY % |
|---|---|---|---|---|---|---|
| 0 | 94.5 | 75.7 | 6.4 | 16.4 | 1.4 | 0 |
| 2 | 93.1 | 77.7 | 5.5 | 15.6 | 1.1 | 0 |
| 4 | 92.5 | 77.9 | 5.4 | 15.7 | 1 | 0 |
| 6 | 92.2 | 77.9 | 5.3 | 15.8 | 0.8 | 0 |
| 10 | 91.6 | 77.6 | 5.4 | 16.2 | 0.8 | 0 |
| 14 | 91.2 | 77.5 | 5.4 | 16.3 | 0.8 | 0 |
| 16 | 91.2 | 77.5 | 5.4 | 16.3 | 0.8 | 0 |
| 18 | 90.9 | 77.6 | 5.3 | 16.2 | 0.8 | 0 |
| 23 | 90.4 | 77.1 | 5.5 | 16.6 | 0.7 | 0 |
| 63 | 89.0 | 76.6 | 6.0 | 16.8 | 0.5 | 0 |

TABLE 2

| TIME hours | CONVERSION % | MAA SELECTIVITY % | PROPENE SELECTIVITY % | ACETONE SELECTIVITY % | ACETIC ACID SELECTIVITY % | $CO/CO_2$ SELECTIVITY % |
|---|---|---|---|---|---|---|
| 0 | 91.5 | 72.3 | 10.5 | 16.2 | 0.9 | 0 |
| 2 | 89.2 | 72.2 | 10.4 | 16.7 | 0.6 | 0 |
| 4 | 89.4 | 73.3 | 10.1 | 16.1 | 0.5 | 0 |
| 6 | 90.9 | 72.9 | 10.1 | 16.4 | 0.8 | 0 |
| 8 | 90.5 | 73 | 10.1 | 16.4 | 0.4 | 0 |
| 10 | 93.3 | 73 | 9.5 | 16.9 | 0.5 | 0 |
| 12 | 90 | 72.7 | 8.7 | 17.7 | 0.8 | 0 |

TABLE 3

| TIME hours | CONVERSION % | MAA SELECTIVITY % | PROPENE SELECTIVITY % | ACETONE SELECTIVITY % | ACETIC ACID SELECTIVITY % | $CO/CO_2$ SELECTIVITY % |
|---|---|---|---|---|---|---|
| 0 | 81.9 | 70.6 | 6.4 | 21 | 1.3 | 0 |
| 3 | 86.3 | 72.6 | 5.9 | 20.2 | 1.1 | 0 |
| 4 | 86 | 72.5 | 6.1 | 20.3 | 1.1 | 0 |
| 5 | 82 | 72.7 | 6.1 | 20.2 | 1 | 0 |
| 7 | 81 | 73.3 | 6.1 | 19.8 | 0.9 | 0 |
| 9 | 78.6 | 72.6 | 5.9 | 19.8 | 0.8 | 0 |
| 11 | 79.3 | 72.7 | 6.4 | 20.0 | 0.8 | 0 |
| 13 | 73.6 | 72.4 | 6.4 | 20.3 | 0.8 | 0 |
| 15 | 76.4 | 72.5 | 6.4 | 20.2 | 0.8 | 0 |
| 17 | 72.6 | 72.4 | 6.5 | 20.1 | 0.8 | 0 |

TABLE 4

| TIME hours | CONVERSION % | MAA SELECTIVITY % | PROPENE SELECTIVITY % | ACETONE SELECTIVITY % | ACETIC ACID SELECTIVITY % | $CO/CO_2$ SELECTIVITY % |
|---|---|---|---|---|---|---|
| 0 | 93.1 | 77.15 | 8.2 | 12.2 | 1.1 | 0.8 |
| 1 | 93.7 | 79.6 | 7.8 | 10.6 | 1 | 0.5 |
| 2 | 93.7 | 79.7 | 7.8 | 10.4 | 1 | 0.6 |
| 3 | 93.5 | 79.4 | 7.8 | 10.5 | 1 | 0.7 |
| 5 | 93.4 | 79.2 | 7.8 | 10.5 | 1 | 1 |
| 6 | 93.2 | 78.6 | 8.3 | 11.9 | 0.6 | 0.8 |
| 8 | 93.3 | 79.4 | 7.8 | 10.3 | 1 | 1 |
| 25 | 92.7 | 79 | 8 | 10.4 | 0.9 | 1.1 |

TABLE 5

| TIME hours | CONVERSION % | MAA SELECTIVITY % | PROPENE SELECTIVITY % | ACETONE SELECTIVITY % | ACETIC ACID SELECTIVITY % | $CO/CO_2$ SELECTIVITY % |
|---|---|---|---|---|---|---|
| 0.5 | 91.9 | 77.6 | 7.4 | 12.6 | 2.6 | 0 |
| 1 | 91.9 | 76.4 | 6.7 | 12 | 2.2 | 2.6 |
| 3 | 91.2 | 76.9 | 6.6 | 12.2 | 6.6 | 2.3 |
| 5 | 90.9 | 77.3 | 6.3 | 12.4 | 6.3 | 2.1 |
| 7 | 91.2 | 77.6 | 6.5 | 12.1 | 1.8 | 2 |
| 9 | 91.7 | 77.8 | 6.2 | 12.4 | 1.7 | 1.9 |
| 11 | 91.4 | 77.9 | 6.3 | 12.4 | 1.7 | 1.7 |

TABLE 6

| TIME hours | CONVERSION % | MAA SELECTIVITY % | PROPENE SELECTIVITY % | ACETONE SELECTIVITY % | ACETIC ACID SELECTIVITY % | $CO/CO_2$ SELECTIVITY % |
|---|---|---|---|---|---|---|
| 2 | 81 | 75.5 | 7.8 | 14.8 | 0.7 | 1.1 |
| 3 | 81.2 | 75.8 | 7.8 | 14.7 | 0.7 | 1 |

TABLE 6-continued

| TIME hours | CONVERSION % | MAA SELECTIVITY % | PROPENE SELECTIVITY % | ACETONE SELECTIVITY % | ACETIC ACID SELECTIVITY % | CO/CO$_2$ SELECTIVITY % |
|---|---|---|---|---|---|---|
| 5 | 79.6 | 74.6 | 8.4 | 15.5 | 0.7 | 0.9 |
| 7 | 78.4 | 74.5 | 8.4 | 15.6 | 0.7 | 0.8 |
| 10 | 79.3 | 75 | 8.4 | 15.4 | 0.6 | 0.6 |
| 12 | 78.3 | 74.3 | 8.6 | 15.9 | 0.6 | 0.6 |
| 15 | 79.4 | 74.5 | 8.7 | 15.7 | 0.6 | 0.5 |

TABLE 7

| TIME hours | CONVERSION % | MAA SELECTIVITY % | PROPENE SELECTIVITY % | ACETONE SELECTIVITY % | ACETIC ACID SELECTIVITY % | CO/CO$_2$ SELECTIVITY % |
|---|---|---|---|---|---|---|
| 0 | 85.2 | 76.3 | 6.9 | 14.2 | 1.5 | 1.1 |
| 1 | 84.9 | 76.4 | 6.6 | 14 | 1.2 | 1.7 |
| 3.5 | 85 | 76.5 | 6.8 | 14.7 | 1 | 1.1 |
| 6 | 80.6 | 76.9 | 6.4 | 15.6 | 0.8 | 0.3 |
| 8.5 | 86.6 | 76.2 | 6.9 | 15 | 0.9 | 1 |
| 11 | 80.1 | 75.5 | 6.9 | 15.1 | 0.8 | 1.8 |
| 14.5 | 77.6 | 76.6 | 6.3 | 16.3 | 0.7 | 0 |
| 17 | 83.7 | 76.3 | 7.7 | 16.6 | 0.8 | 0.5 |
| 19.5 | 80.4 | 77.0 | 7 | 15.3 | 0.8 | 0 |
| 22 | 80.2 | 76.1 | 6.9 | 15.5 | 0.8 | 0.8 |
| 24.5 | 80.2 | 76.1 | 7.1 | 14.9 | 0.8 | 1 |

TABLE 8

| TIME hours | CONVERSION % | MAA SELECTIVITY % | PROPENE SELECTIVITY % | ACETONE SELECTIVITY % | ACETIC ACID SELECTIVITY % | CO/CO$_2$ SELECTIVITY % |
|---|---|---|---|---|---|---|
| 0.2 | 96.1 | 71.3 | 8 | 16.9 | 1.7 | 2.5 |
| 1 | 92.6 | 72 | 5.8 | 17.7 | 1.1 | 1.4 |
| 4 | 90.8 | 71.6 | 7.3 | 18.6 | 0.7 | 1.1 |
| 5 | 90.9 | 71.5 | 7.5 | 18.4 | 0.8 | 1 |
| 11 | 90.2 | 69.9 | 8.6 | 18.3 | 1 | 1.3 |
| 18 | 90 | 69.7 | 9 | 18.2 | 1.1 | 0.9 |
| 26 | 88.5 | 69.4 | 9 | 18.3 | 0.6 | 1 |
| 27 | 88.4 | 70.2 | 8.1 | 18.1 | 0.7 | 1.1 |

Without further elaboration, it is believed that one skilled in the art can, using the preceding description, utilize the present invention to its fullest extent. The preferred specific embodiments are, therefore, to be construed as merely illustrative, and not limitative of the disclosure in any way whatsoever.

The entire disclosure of all applications, patents and publications, cited above, and of corresponding French application 91-10868, are hereby incorporated by reference.

The preceding examples can be repeated with similar success by substituting the generically or specifically described reactants and/or operating conditions of this invention, and without departing from the spirit and scope thereof, can make various changes and modifications of the invention to adapt it to various usages and conditions.

We claim:

1. A catalytic system based on oxygen, vanadium, phosphorus and molybdenum, of the formula:

$$H_mX_nMe_pPMO_{12-x}V_xO_{40}$$

wherein
X represents a VO$^{2+}$ cation with $0<n\leq2$,
H represents protons with $0\leq m<4$, $0\leq x\leq3$,
Me is a metal ion, with $0\leq p<t$, t depending on the charge of the corresponding ion.

2. A catalytic system according to claim 1, wherein Me is an ion of a transition metal, magnesium, or an alkali metal.

3. A catalytic system according to claim 2, wherein Me is copper, cobalt, iron, silver, nickel, manganese or magnesium.

4. In a process for manufacturing the catalytic system such as defined in claim 1, comprising providing $H_4PMo_{12-x}V_xO_{40}$ and introducing VO$^{2+}$ cation and, optionally, at least one Me cation, wherein the VO$^{2+}$ cation and the optional Me cation are introduced by further reaction with barium hydroxide and vanadyl sulfate and, optionally, at least one sulfate of at least one Me cation to precipitate barium sulfate, and the resultant barium sulfate is separated from the resultant reaction product.

5. In an oxydehydrogenation reaction of a saturated carboxylic acid to form an $\alpha,\beta$-unsaturated carboxylic acid, the improvement comprising conducting the reaction with a catalytic system according to claim 1.

6. In an oxidation reaction of aldehydes to acids, the improvement comprising conducting the reaction with a catalytic system according to claim 1.

7. A process according to claim 4, wherein the reaction product contains hdyrogen and further comprising substituting at least a part of the hydrogen in the reaction product of claim 4 by reaction with a carbonate or hydroxide of the corresponding Me cation.

8. A catalytic system according to claim 1, wherein Me is an alkali metal.

9. A catalyst system according to claim 1, being VOH$_2$PMO$_{11}$VO$_{40}$.

10. A catalyst system according to claim 1, being (VO)$_{0.5}$H$_3$PMO$_{11}$VO$_{40}$.

11. A catalyst system according to claim 1, being (VO)$_2$PMo$_{11}$VO$_{40}$.

12. A catalyst system according to claim 1, being (VO)$_{1.5}$PMo$_{11}$VO$_{40}$.

13. A catalyst system according to claim 1, being VOHCu$_{0.5}$PMo$_{11}$VO$_{40}$.

14. A catalyst system according to claim 1, being VOHCo$_{0.5}$PMo$_{11}$VO$_{40}$.

15. A catalyst system according to claim 1, being VOHFe$_{0.33}$PMo$_{11}$VO$_{40}$.

16. A catalyst system according to claim 1, being VOH$_2$PMo$_{11}$VO$_{40}$.

17. A catalyst system according to claim 1, being VOHCu$_{0.5}$PMo$_{11}$VO$_{40}$.

18. A process according to claim 4, wherein at least one Me cation is introduced into the reaction product.

19. A process according to claim 5, comprising bringing said saturated carboxylic acid in the vapor phase into contact with a gas comprising oxygen in a molar ratio of oxygen to the saturated acid not exceeding 5 to form a charge and reacting said charge at a reaction temperature of between 280°-400° C. in the presence of said catalytic system.

20. A process according to claim 19, wherein the reaction is conducted in the presence of water vapor.

21. A process according to claim 19, wherein said gaseous charge comprises saturated acid, molecular oxygen, optionally water, and an inert gaseous diluent, the molar percentage of acid in said mixture being between 1 and 8%, the molar proportion of molecular oxygen being 0.2 to 5 times greater than that of the saturated acid, the water being introduced into the reactor at a molar ratio between 0 and 15, inclusive, with respect to the saturated acid.

22. A process according to claim 19, wherein the charge and the catalyst are contacted for a reaction time of between 0.1 and 50 seconds.

23. A process according to claim 19, wherein the saturated carboxylic acid is isobutyric acid, which is oxydehydrogenated into methacrylic acid.

24. A process according to claim 6, bringing said aldehyde in the vapor phase into contact with a gas comprising molecular oxygen in a molar ratio of oxygen to the aldehyde not exceeding 5 to form a charge and reacting said charge at a reaction temperature between 280° C. and 400° C. in the presence of said catalytic system.

25. A process according to claim 24, wherein the reation is conducted in the presence of water vapor.

26. A process according to claim 24, wherein said gaseous charge comprises an aldehyde, molecular oxygen, optionally water, and an inert gaseous diluent, the molar percentage of aldehyde in the mixture between 1 and 8%, the molar proportion of molecular oxygen being 0.2 to 5 times greater than that of the aldehyde, the water being introduced into the reactor at a molar ratio between 0 and 15, inclusive, with respect to the aldehyde.

27. A process according to claim 24, wherein the charge and the catalyst are contacted for a reaction time of between 0.1 and 50 seconds.

28. A process according to claim 24, wherein the aldehyde is methacrolein, which is oxidized into methacrylic acid.

29. A process according to claim 5, wherein Me is an ion of magnesium, an alkali metal, copper, cobalt, iron, silver, nickel, or manganese.

30. A process according to claim 6, wherein Me is an ion of magnesium, an alkali metal, copper, cobalt, iron, silver, nickel, or manganese.

* * * * *